United States Patent [19]

Schweizer et al.

[11] 4,037,967
[45] July 26, 1977

[54] APPARATUS FOR MEASURING THE DENSITY OF A LIQUID, UTILIZING THE LAW OF REFRACTION

[75] Inventors: Walter Schweizer, Berlin; Martin-Ulrich Reissland, Gummersbach, both of Germany

[73] Assignee: VDO Adolf Schindling AG, Frankfurt am Main, Germany

[21] Appl. No.: 465,241

[22] Filed: Apr. 29, 1974

[30] Foreign Application Priority Data

May 14, 1973 Germany .......................... 2324259

[51] Int. Cl.² .......................................... G01N 21/46
[52] U.S. Cl. ................................................ 356/135
[58] Field of Search .............................. 356/128–137

[56] References Cited

U.S. PATENT DOCUMENTS

| 2,474,044 | 6/1949 | Forrest | 356/137 |
| 2,972,926 | 2/1961 | Goldberg et al. | 356/135 |

*Primary Examiner*—John K. Corbin
*Assistant Examiner*—Conrad Clark
*Attorney, Agent, or Firm*—Otto John Munz

[57] ABSTRACT

An apparatus for continuously measuring the density of a liquid within prespecified limits, utilizing the law of refraction, particularly an apparatus for measuring the acid density of a motor vehicle storage battery for the purpose of determining its state of charge. The apparatus has an optical system with a photosensitive element and a light transmissive body with a measuring surface which is in contact with the liquid, and with a light source which illuminates the measuring surface.

The light source has an illuminated surface with a non-directional transmission.

The illuminated surface facing the measuring surface is spaced therefrom.

The illuminating surface together with said measuring surface define an open container filled with the said liquid. A frosted glass disc illuminated by a lamp forms the illuminated surface.

The optical system contains a convergent lens whose main plane, together with the measuring surface encloses a precisely defined acute angle.

13 Claims, 2 Drawing Figures

APPARATUS FOR MEASURING THE DENSITY OF A LIQUID, UTILIZING THE LAW OF REFRACTION

BACKGROUND OF THE INVENTION

1. Field of the Invention

The invention relates to a refraction meter with reflective optical system.

2. Description of the Prior Art

U.S. Pat. No. 2,483,102 — R.M. Pierson, Sept. 9, 1949;

For: Refractometer employing photosensitive devices; and

U.S. Pat. No. 2,569,127 — G.C. Eltenton Sept. 25, 1951;

For: Refractive Index Measurement of Fluids, are made of record.

For the purpose of measuring the density of a liquid, an apparatus is already known, comprising a glass rod immersed in the liquid to be measured. In such a structure, at the glass rod end that projects from the liquid, there is a light source that produces a pencil of light rays which enters parallel to the optical axis of the glass rod, and at the immersed glass rod end there are two deflecting surfaces and a measuring surface. These surfaces are arranged in such a way that the light pencil passes, by way of one of the deflecting surfaces, to the measuring surface under the angle of total reflection at the lowest occuring density, and therefrom, by way of the other deflection surface, to a viewing scope. Such an apparatus presents the disadvantage that the density of the liquid can be determined only within very narrow limits and only subjectively. A continuous dependable measurement of the density of liquids by means of this apparatus is therefore not possible.

Another known apparatus provides for a light transmissive, rod-shaped body. In this structure, at the end that is immersed in the liquid is a front surface perpendicular to the longitudinal axis. The surface is provided with a reflecting coat, and at the end that projects from the liquid are provided a light source and a photosensitive element. In such an apparatus, the light rays entering the body are refracted into the liquid to a greater or smaller extent, depending on the density of the liquid, so that the quantity of light that passes into the liquid is a criterion for the density of the liquid. Such an apparatus, on the one hand, makes a continuous measurement possible. Care must be taken, however, that the depth of the immersion of the body remains always the same, since otherwise substantial errors of measurement may result. Since, however, especially in storage batteries, the liquid level varies considerably, such an apparatus cannot be used for measuring the acid density of a storage battery.

Another apparatus for measuring the acid density of a storage battery has become known wherein a pencil of rays departing from a light source is directed, through a prism filled with the liquid, toward several photosensitive receivers. Depending on the density of the liquid, the pencil of rays is refracted to a greater or smaller extent by the prism and therefore strikes the photosensitive receiver associated with the said index of refraction according to the index of refraction prevailing at each instant. Such an apparatus presents the disadvantage that it has a large volume and cannot be installed in the battery casing without extensive alterations thereon.

Moreover, this apparatus employs expensive structural parts and is therefore itself expensive.

SUMMARY

The objects of the invention are:

to overcome the difficulties and disadvantages of the prior art;

to produce an apparatus which permits a continuous measurement of the density of a liquid, independently of the liquid level temporarily prevailing and simultaneously represents an inexpensive structure, that does not require many parts, is of small volume and permits ease of assembly;

to provide an optical system equipped with a light source, constructed as an illuminated surface with a preferably high degree of a non-directional transmission; and a measuring surface spaced a short distance from the illuminated surface and defining jointly with the measuring surface a container open at least on one side, filled with the liquid;

to provide such an apparatus operable according to the principle of a grazing or touching light entry, whereby the light rays penetrating the liquid strike the measuring surface under an angle with respect to the normal surface which preferably is smaller than, or at most equal to a 90° angle;

to reproduce the light refracted into the light transmissive body on the measuring surface on a screen as a brightly illuminating surface;

to arrange a photo-sensitive element in the screen plane controllably by the boundary between light and dark areas of this surface, which boundary changes its position depending on the liquid density;

to control a photosensitive element arranged in the screen plane;

to carry out measurements of the density of the liquid independently of the liquid level prevailing at each instance when the space filled by the liquid is located below the minimum liquid level, which condition can, as demonstrated below, be fulfilled without difficulties;

to provide such an apparatus, which can be manufactured inexpensively in an extremely compact form and with a small number of structural parts, giving, nevertheless an excellent performance as an acid density measuring device for storage batteries.

BRIEF DESCRIPTION OF THE DRAWINGS

The invention will be explained with the aid of the following drawings; presented by way of example.

DESCRIPTION OF THE PREFERRED EMBODIMENTS

Figure 1:
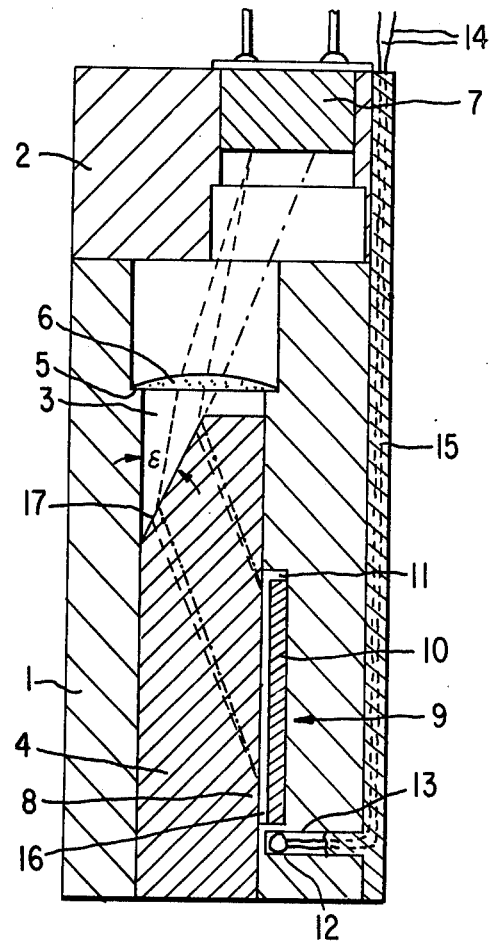
FIG. 1 is a diagrammatic cross-sectional view of one embodiment of the measuring apparatus of the invention with a convergent lens.

In a preferred embodiment, the illuminated surface of the apparatus of the invention is represented by a disc of frosted glass illuminated by a light source such as a lamp. Such a device presents substantial manufacturing advantages employing other possible parts, such as a parallel pencil of light rays directed toward the measuring surface at a super-arcuate angle.

The disc of frosted glass may be suitably of a siliconized glass. Such a type of glass can be manufactured with a predominantly non-directed degree of transmission of about 92%, so that it is particularly suitable for the present purposes. Furthermore, an arrangement of the lamp in the area of one of the front sides of the discs of frosted glass in accordance with this invention has proved to be practical. In such an arrangement, the light rays which enter the measuring surface in an approximately grazing or touching manner are of the highest intensity, and the boundary between light and dark is particularly distinct.

It is advantageous to use as the light source a gallium arsenide diode. This results in a particularly small volume of the apparatus. Moreover, a gallium arsenide diode, in contrast to an incandescent lamp, which may likewise be employed, has a lower power requirement and a longer life.

A photoelement, a photodiode, or a photoresistor which is particularly advantageous with regard to photosensitivity and cost, may be used.

In order to obtain a sharply defined reproduction of the boundary between the dark and the light areas in the screen plane which coincides with the effective surface of the photosensitive element or is substituted thereby, the optical system contains most suitably a convergent lens whose main plane encloses jointly with the measuring surface, an acute angle in order to reduce spherical aberration.

According to a further concept of the invention, such a convergent lens may be dispensed with if the measuring surface is adjoined by an opaque layer and the photosensitive element is arranged in such a manner that only light rays that are refracted into the photoconductive body in the area of the end of the opaque layer strike the photosensitive element. This results in a blurred boundary between dark and light, and consequently in a certain power loss in comparison to an apparatus with a convergent lens. Since, however, such power loss can be compensated conventionally by modifying the amplification of an operation amplifier series-connected to the photosensitive element, the advantages of such an apparatus, namely an extremely small structural volume, simplicity of manufacture, and the saving of a lens, are predominant.

When only small density changes occur, especially in the acid of storage batteries, the position change of the boundary between dark and light areas in the apparatus of the invention is relatively small.

According to a further concept of the invention, this position change of the said boundary can be increased by providing at the end of the light transmissive body that faces the photosensitive element a boundary surface that causes a refraction of the pencil of light rays arriving from the measuring surface. This boundary surface is inclined with respect to the measuring surface by the angle $$\epsilon = \arc\sin \frac{\hat{n}}{N} - \arc\sin \frac{n_o}{N}$$

in which formula $\hat{n}$ is the largest occurring index of refraction of the liquid, $n_o$ the index of refraction of the medium positioned between the light transmissive body and the photosensitive element, and $N$ the index of refraction of the photoconductive body. The increase of the range of motion of the boundary between dark and light areas which can be achieved thereby, results in a higher resolution and has the advantage that the demands upon an accurate position of the photosensitive element in the optical system are considerably lower.

Figure 2:
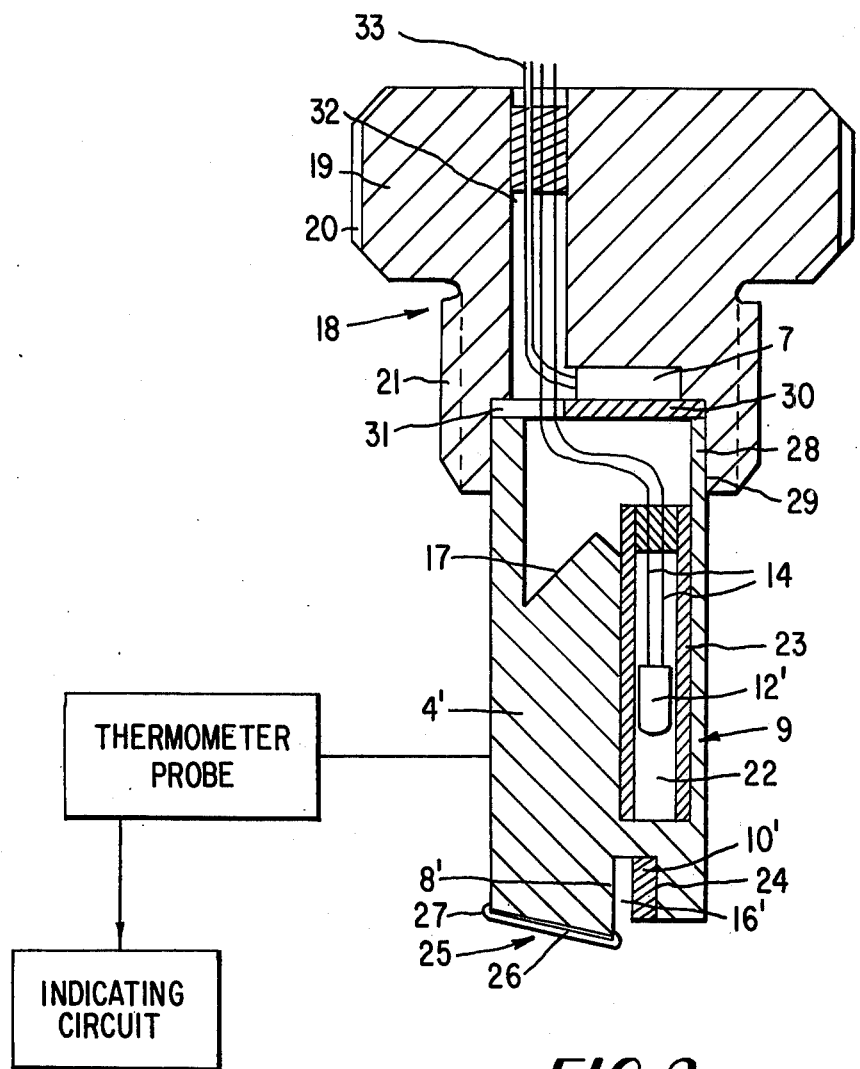
FIG. 2 is a diagrammatic cross-sectional view of another embodiment of the measuring apparatus of the invention with a limited measuring surface in the form of a battery closure plug.

In the embodiment of FIG. 2 preferred for the measurement of acid density in a storage battery, the light transmissive body is shaped as a rod in which the light source is mounted and which is provided, at one end, with a measuring surface and which changes at its other end into a battery closure plug, in which is mounted the photosensitive element. This embodiment of the apparatus requires no structural changes in the battery casing and no additional means for fastening the device to the battery casing.

Consequently, the mounting of the apparatus at the battery casing can be carried out by unskilled personnel and thus also by an inexperienced motorist himself. Therefore this second embodiment is excellently suited for complementing already existing storage batteries mounted in the motor vehicle.

An opaque layer is employed to restrict the measuring surface in this embodiment. A deflecting surface is used as the opaque layer. It is arranged in the path of rays, behind the measuring surface and restricts one side of the measuring surface. By these means is achieved a particularly compact structure of the apparatus. By suitable positioning of the deflecting surface relative to the measuring surface, the transitional area from light to dark can be made very narrow.

In order to improve the reflecting properties, the deflecting surface is provided with a reflecting layer, which in turn is covered with a protective layer against the liquid. In an apparatus for measuring the acid density of a storage battery, bitumen may be employed for such a protective layer. The reflecting layer may comprise silver, aluminum, or gold. In connection with a gallium arsenide diode or with an incandescent lamp operated at low voltage, a gold layer presents the advantage that it has an extremely high degree of reflection for the spectrum of the light emanating from such a light source. Besides, the protective layer in this case need not to be acidproof since gold is insoluble in sulfuric acid.

The measuring apparatus of FIG. 1 is shown in a longitudinal section, and comprises a casing 1 with a cover 2, both made of an opaque material, such as inked polymethyl-metacrylate. The casing and the cover each has a rectangular cross-section. The casing is provided with a rectangular recess 3 which extends in the direction of the longitudinal axis through the casing, and forms a sheath for a rod-shaped, light transmissive body 4, preferably also made of polymethyl-metacrylate, which is sheathed therein. To insure a safe fixed mounting of the light transmissive body in the casing, the two parts are integrally joined together. A convergent lens 6 is inserted in a recess 3, which is widened at the end facing the cover, forming a shoulder 5. The convergent lens rests on the shoulder and is glued together therewith. A photoresistor 7 is arranged in the path of rays behind the lens.

A portion of a lateral surface of the light transmissive body forms the measuring surface 8 of the apparatus. Opposite from the measuring surface is arranged a light source. The light source has a frosted glass disc 10 of siliconized glass, located in a recess 11 which extends transversely through the entire casing 1. A small incandescent lamp 12 is mounted in the area of the lower front of the frosted glass disc in a transverse hole 13. Feed lines 14 passing upward from the transverse hole are protected by a bituminous protective layer 15. The transverse hole is also sealed acidproof by a protective layer 15.

The thickness of the frosted glass disc and the depth of the recess 11 are adjusted relative to each other so that a narrow space 16 is formed between the surface, facing the measuring surface of the frosted glass disc, and the measuring surface 8. This space is completely filled with the acid (i.e. the liquid whose density is to be measured).

Since the extreme values of the acid density of a lead storage battery vary within a relatively narrow range only (the indices of refraction assigned to the extreme values vary between $\hat{n} = 1.364$ and $\hat{n} = 1.380$), there results only a small change of position of the boundary between the dark and the light areas. To increase this change of position, a boundary surface 17 is provided at the end, facing the convergent lens of the light transmissive body. The boundary surface causes a refraction of the light rays emanating from the measuring surface 8. This boundary surface 17 is inclined with respect to the measuring surface 8 by an angle of 25.69°. This angle can be computed by means of the equation indicated above, basing the computation on the values $\hat{n} = 1.38$, $N = 1.49$, (index of refraction of polymethyl-metacrylate) and $n_o = 1$ (index of refraction of the air space adjacent to boundary surface 17).

In this embodiment of the measuring apparatus, the light rays directed under a flat angle, through the space 16 filled with acid, against the measuring surface 8 are refracted into the light transmissive body 4. After another refraction at the boundary surface 17, they pass to the convergent lens 6 and therefrom to the photoresistor 7.

The course of the adjacent-to-the-boundary light rays refracted at the lower acid density limit under the limiting angle for total reflection, into the light transmissive body 4 is shown in dash lines, and the course of the adjacent-to-the-boundary light rays refracted at the upper acid density limit under the limiting angle for total reflection, into the light transmissive body 4, is shown in dash-and-dot lines. The change of the position of the boundary between dark and light areas can be distinctly recognized on the receiver.

The apparatus of FIG. 2, is shown in a longitudinal section and is provided for measuring the acid density in a lead storage battery. It contains a rod-shaped photoconductive body 4', with one of its ends fixed in a part 18 shaped as a battery closure plug conventionally made of inked polymethyl metacrylate or equivalents. The closure plug element comprises a head 19, having a periphery provided with a milled edge 20, and a threaded pin 21.

In the light transmissive body 4' is provided an oblong recess 22, concentric to the body axis. The recess holds a gallium arsenide diode 12' and an opaque screen in the form of a metallic pipe section 23. The light transmissive body at its free end is provided with an indentation 24. One of the lateral surfaces of the indentation serves as the measuring surface 8', while at the other lateral surface is mounted a frosted glass disc 10' of siliconized glass. The width of the indentation is chosen so that it accommodates a front side of the frosted glass disc 10' in the area of the pencil of light rays produced by the gallium arsenide diode 12' and, also provides a space 16' between the frosted glass disc and the measuring surface 8', into which the acid can penetrate and which the acid can fill completely. The measuring surface is enclosed, on the one hand, by the base surface of the indentation 24 and, on the other hand, by a deflecting surface 25 molded on the light transmissive body 4'. The deflecting surface 25 is provided with a reflecting layer 26 of gold. The reflecting layer 26 is protected by a bituminous layer 27 against the acid.

At the end facing away from the measuring surface, the light transmissive body 4' changes to a caselike terminal section 28 which is firmly mounted in a corresponding recess 29 in a threaded pin 21. Between the terminal section 28 and the closure plug element 18 is arranged a frosted glass disc 30 upon which rests the photoresistor 7. The frosted glass disc is provided with a perforation 31 for the passage of electrical conduit lines 14 for the gallium arsenide diode 12'. Likewise a perforation 32 is provided in the closure plug ement 18 for the lines 14 and the connection lines of the photoresistor 7.

In this measuring apparatus light rays refracted from the frosted glass disc 10' into the acid and directed against the lower limit of measuring surface 8', are guided over the reflecting layer 26 and the boundary surface 17 upon the photoresistor 7. The blurred boundary between the dark and the light areas thereby produced leads to a certain power loss when compared to the measuring apparatus of the first embodiment. The power loss, however, is compensated by the electronic part of the apparatus.

As is known, the density of the acid in a storage battery is a function of the temperature: it decreases when the temperature rises. Since, however, the viscosity of the acid likewise decreases at a rising temperature and this effect outweights the other, the acid of the battery yields a greater amount of charge at increasing temperature in spite of decreasing density. According to a further concept of the invention, this dependency is taken into account by providing, on or in the portion of the apparatus that is immersed in the liquid, a thermometer probe, the output signal of which is fed to an indicating circuit as a corrective value.

What is claimed is:

1. Apparatus for continuously measuring the density of a liquid within predetermined limits by use of the law of refraction, said apparatus being particularly useful for measuring the density of the electrolytic acid in a motor vehicle storage battery in order to determine its state of charge, comprising:

A. a light-transmissive body having a measuring surface thereon,
   B. a plate of frosted light-transmissive material comprising at least one frosted surface and at least one edge, the frosted surface being mounted in a position facing the measuring surface and spaced therefrom,
   C. a lamp for directing light into the edge of said plate to cause the frosted surface to function as an illuminating surface of a light source with non-directional light transmissive characteristics,
   D. the illuminating surface and the measuring surface defining walls of an open chamber which is filled with the liquid, and
   E. a photosensitive element placed to receive light deflected by the measuring surface,
   F. said measuring surface being enclosed by an opaque layer, and the light-transmissive body being arranged relative to the direction of rays emanating from said light source, so that only the light rays refracted in the area of the end of the opaque layer into the light-transmissive body strike the photosensitive element.

2. Apparatus for continuously measuring the density of a liquid as claimed in claim 1, for measuring the acid density of a storage battery, said light-transmissive body being constructed as a rod, said light source being arranged adjacent said rod, a measuring surface being provided at one end of said rod, said rod changing at its other end to a battery closure plug, said photosensitive element being mounted in the plug.

3. Apparatus for continuously measuring the density of a liquid as claimed in claim 1, said lamp being a gallium arsenide diode.

4. Apparatus for continuously measuring the density of a liquid as claimed in claim 1, said photosensitive element being photoresistor.

5. Apparatus for continuously measuring the density of a liquid as claimed in claim 1, further comprising thermometer probe provided with the portion of the apparatus that is immersed in the liquid.

6. Apparatus according to claim 1, further comprising a convergent lens having a main plane, which plane, together with the measuring surface, forms an acute angle.

7. Apparatus according to claim 1 wherein the frosted light-transmissive material comprises frosted glass.

8. Apparatus according to claim 7, wherein the frosted glass is siliconized.

9. Apparatus for continuously measuring the density of a liquid within predetermined limits by use of the law of refraction, said apparatus being particularly useful for measuring the density of the electrolytic acid in a motor vehicle storage battery in order to determine its state of charge, comprising:
   A. a light-transmissive body having a measuring surface thereon,
   B. a plate of frosted light-transmissive material comprising at least one frosted surface and at least one edge, the frosted surface being mounted in a position facing the measuring surface and spaced therefrom,
   C. a lamp for directing light into the edge of said plate to cause the frosted surface to function as an illuminating surface of a light source with non-directional light transmissive characteristics,
   D. the illuminating surface and the measuring surface defining walls of an open chamber which is filled with the liquid,
   E. a photosensitive element placed to receive light deflected by the measuring surface,
   said measuring surface being enclosed by an Opaque layer, and the light-transmissive body being arranged relative to the direction of rays emanating from said light source, so that only the light rays refracted in the area of the end of the opaque layer into the light-transmissive body strike the photosensitive element, and
   F. a deflecting surface provided as the opaque layer arranged in the path of rays behind the said measuring surface and limiting one side of the measuring surface.

10. Apparatus for continuously measuring the density of a liquid as claimed in claim 9, said deflecting surface being provided with a reflecting layer covered with a protective layer.

11. Apparatus for continuously measuring the density of a liquid as claimed in claim 10, said reflecting layer comprising a gilded surface.

12. Apparatus for continuously measuring the density of a liquid within predetermined limits by use of the law of refraction, said apparatus being particularly useful for measuring the density of the electrolytic acid in a motor vehicle storage battery in order to determine its state of charge, comprising:
   A. a light-transmissive body having a measuring surface thereon,
   B. a plate of frosted light-transmissive material comprising at least one frosted surface and at least one edge, the frosted surface being mounted in a position facing the measuring surface and spaced therefrom,
   C. a lamp for directing light into the edge of said plate to cause the frosted surface to function as an illuminating surface of a light source with non-directional light transmissive characteristics,
   D. the illuminating surface and the measuring surface defining walls of an open chamber which is filled with the liquid,
   E. a photosensitive element placed to receive light deflected by the measuring surface,
   said light-transmissive body being constructed as a rod, said light source being arranged adjacent said rod; a measuring surface being provided at one end of said rod, said rod changing at its other end to a battery closure plug, said photosensitive element being mounted in the said plug; said measuring surface being enclosed by an opaque layer, and the light-transmissive body being arranged relative to the direction of rays emanating from said light source, so that only the light rays refracted in the area of the end of the opaque layer into the light-transmissive body strike the photosensitive element, and
   F. a deflecting surface provided as the opaque layer arranged in the path of rays behind the said measuring surface and limiting one side of the said measuring surface.

13. Apparatus for continuously measuring the density of a liquid within predetermined limits by use of the law of refraction, said apparatus being particularly useful for measuring the density of the electrolytic acid in a motor vehicle storage battery in order to determine its state of charge, comprising:
   A. a light-transmissive body having a measuring surface thereon,
   B. a plate of frosted light-transmissive material comprising at least one frosted surface and at least one edge, the frosted surface being mounted in a position facing the measuring surface and spaced therefrom,
   C. a lamp for directing light into the edge of said plate to cause the frosted surface to function as an illuminating surface of a light source with non-directional light transmissive characteristics,
   D. the illuminating surface and the measuring surface defining walls of an open chamber which is filled with the liquid,
   E. a photosensitive element placed to receive light deflected by the measuring surface, and
   F. a boundary surface for a refraction of the pencil of light rays arriving from the measuring surface, at the end of the light-transmissive body that faces the photosensitive element, said boundary surface being inclined, with respect to the measuring surface by an angle E, given by formula $$\hat{\epsilon} = \arc\sin\frac{n}{N} - \arc\sin\frac{n_o}{N}$$

in which formula $n$ represents the largest occurring index of refraction of the liquid, $n_o$ represents the index of refraction of the medium positioned between the light-transmissive body and the photosensitive element, and $N$ represents the index of refraction of the photoconductive body.

* * * * *